United States Patent [19]

Santeramo

[11] Patent Number: 4,563,178

[45] Date of Patent: Jan. 7, 1986

[54] SYRINGE DOSAGE LIMITER

[76] Inventor: Joseph J. Santeramo, 185 Walnut St., Teaneck, N.J. 07666

[21] Appl. No.: 698,814

[22] Filed: Feb. 6, 1985

[51] Int. Cl.⁴ ............................................. A61J 1/06
[52] U.S. Cl. ...................................... 604/208; 141/27
[58] Field of Search ............... 604/218, 208, 187, 207; 141/2, 27, 95, 21–26

[56] References Cited

U.S. PATENT DOCUMENTS

| | | | |
|---|---|---|---|
| 637,405 | 11/1899 | Papendell | 604/208 |
| 3,045,673 | 7/1962 | Hein | 604/208 |
| 3,337,095 | 8/1967 | Marbach et al. | 604/208 X |
| 4,073,321 | 2/1978 | Moskowitz | 141/27 |
| 4,248,225 | 2/1981 | Moore | 604/208 |

Primary Examiner—John D. Yasko
Attorney, Agent, or Firm—Bacon & Thomas

[57] ABSTRACT

A device for limiting the dosage to be administered by a syringe, including a U-shaped holder defined by a base portion and a pair of leg portions extending therefrom, wherein the base portion includes a slot for detachably securing the handle of a syringe plunger and a pivotal guide detachably securable between the leg portions and selectively displaceable therealong for supporting the syringe barrel in a desired position relative to the syringe plunger.

8 Claims, 6 Drawing Figures

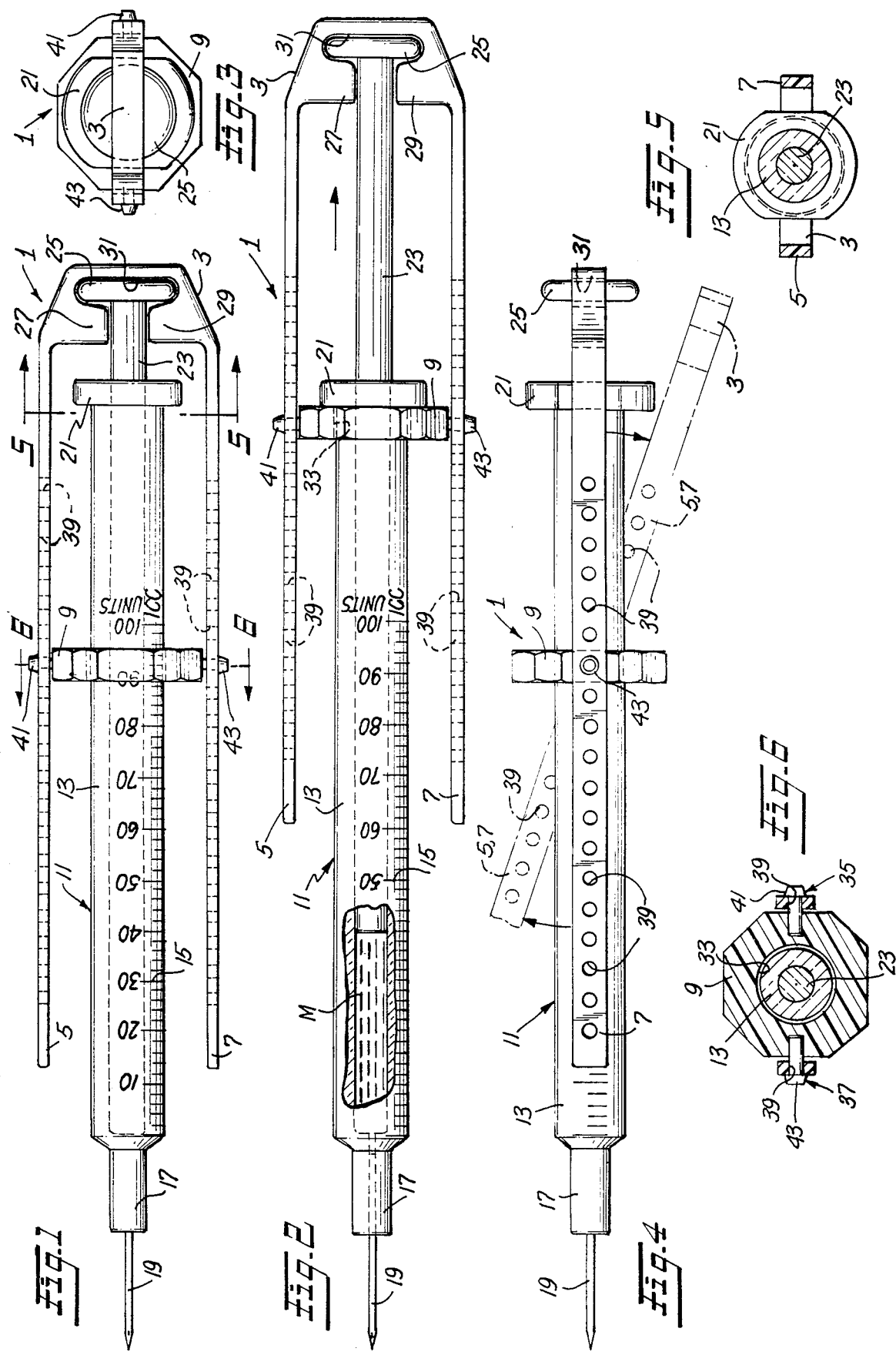

SYRINGE DOSAGE LIMITER

BACKGROUND OF THE INVENTION

1. Field of the Invention

The present invention involves the field of technology pertaining to devices for use in conjunction with a hypodermic syringe for controlling the amount of medication withdrawn and administered by the syringe. More specifically, the invention relates to an improved device for limiting the amount of dosage to be administered by the syringe.

2. Description of the Prior Art

There are many known devices for use in conjunction with a syringe whereby the amount of medication withdrawn by a syringe and administered thereby may be controlled. Such control is of particular importance in preventing an overdose of medication when the syringe injection is intended to be administered by a patient. In this way, medication overdosing by the patient and possible serious consequences resulting therefrom can be avoided.

Several examples of prior art devices for controlling the amount of dosage withdrawn and/or administered by a syringe are disclosed by the Nensel U.S. Pat. No. 2,706,480; Hein U.S. Pat. No. 3,045,673; Wright U.S. Pat. No. 4,219,055; Maki U.S. Pat. No. 4,252,159; and Kontos U.S. Pat. No. 4,267,846.

SUMMARY OF THE INVENTION

It is an object of the present invention to provide an improved device for limiting the amount of medication to be administered by a hypodermic syringe.

It is another object of the invention to provide an improved syringe dosage limiter which is extremely simple in construction and economical to manufacture.

It is a further object of the invention to provide an improved syringe dosage limiter which affords accuracy in operation and is easy to use.

These and other objects of the invention are realized by providing a syringe dosage limiter that includes a U-shaped holder, preferably integrally formed of plastic material, having a slotted base portion for detachably securing the handle of a syringe plunger, and a pair of leg portions extending from the base portion. The leg portions are provided with pairs of opposed corresponding apertures spaced therealong for receiving the outwardly extending axles of a guide member, whereby the guide member may be pivotally secured to and between the leg portions in any desired position therealong by disposing the axles in a selected pair of corresponding apertures. The guide member is provided with a passageway through which the barrel of the syringe is slidably received and supported in a desired position relative to the syringe plunger.

Other objects and advantages of the invention shall become apparent from the following detailed description of a preferred embodiment thereof when considered in conjunction with the drawings wherein like reference characters refer to corresponding parts of the several views.

BRIEF DESCRIPTION OF THE DRAWINGS

FIG. 1 is an enlarged plan view of a syringe dosage limiter according to a preferred embodiment of the invention and shown with a conventional hypodermic syringe engaged therewith;

FIG. 2 is a plan view, partly in section, similar to FIG. 1, but showing the outwardly extending flange of the syringe barrel in engagement with the pivotal guide, and the syringe plunger in an extended position corresponding to a desired dosage;

FIG. 3 is an end view of the syringe dosage limiter and associated syringe of FIG. 1, as seen from the right side thereof;

FIG. 4 is a side elevational view of the syringe dosage limiter and syringe of FIG. 1 shown partly in section and phantom lines depicting the base and leg portions of the limiter in a pivoted position with respect to the guide member, and released from the handle of the syringe plunger;

FIG. 5 is a transverse sectional view taken on the line 5—5 of FIG. 1; and

FIG. 6 is a transverse sectional view taken on the line 6—6 of FIG. 1.

DETAILED DESCRIPTION OF THE PREFERRED EMBODIMENT

A syringe dosage limiter 1, according to a preferred embodiment of the invention, shall now be described with initial reference to FIGS. 1-3. As seen therein, limiter 1 is of a substantially U-shaped configuration defined by a base portion 3 and a pair of leg portions 5 and 7 extending therefrom. A guide member 9 is detachably securable between leg portions 5 and 7, and may also be selectively positioned therealong in a manner to be later described.

Limiter 1 is shown with a conventional hypodermic syringe 11 engaged therewith. Syringe 11 may be of the type that includes a barrel 13 provided with a series of graduation markings 15 therealong for indicating the amount of dosage to be withdrawn and administered. Barrel 13 is provided at one end thereof with a standard fitting 17 for supporting a needle 19. The other end of barrel 13 terminates in an outwardly extending flange 21. A plunger 23 is slidably received within barrel 13 and includes a handle 25 at its outer free end. The manner in which syringe 11 functions to withdraw and administer a dosage of medication is well known in the art and need not be further elaborated herein. Moreover, neither the structure nor function of syringe 11 forms any part of the present invention, and it is in fact possible to utilize any type of syringe device deemed suitable for the practice of the invention as disclosed herein.

As particularly seen in FIG. 3, limiter 1 is of a substantially constant width. Base portion 3 is provided with a pair of inwardly directed ledges 27 and 29 which serve to define in part a slot 31. The spacing between ledges 27 and 29 should correspond to the diameter of plunger 23 so that the latter may be easily passed therebetween. Slot 31 should also be of a configuration and size so as to permit the snug but detachable engagement of handle 25 therein. In this manner, the free end of plunger 23 may be securely retained within base portion 3 by inserting handle 25 within slot 31 and the adjacent portion of plunger 23 between ledges 27 and 29 in the manner shown in FIGS. 1 and 3.

The manner in which barrel 13 of syringe 11 is supported between leg portions 5 and 7 shall now be described. Guide member 9, as seen in FIGS. 3 and 6, is depicted as preferably being of octagonal configuration, but may of course assume any other geometric shape deemed suitable for the practice of the invention. Guide member 9 is provided with a passageway 33 centrally disposed therethrough and corresponding substantially to the diameter of barrel 13 so that the latter may be freely and slidably received therethrough. Guide member 9 is also provided with a pair of outwardly extending axles 35 and 37 on the opposite sides thereof for pivotally securing guide member 9 to leg portions 5 and 7. This is accomplished by providing leg portions 5 and 7 with a plurality of pairs of opposed corresponding apertures 39 spaced therealong. Guide member 9 may therefore be secured to and between leg portions 5 and 7 at any selected position therealong by engaging axles 35 and 37 within the corresponding pair of apertures 39 at that position. As shown in FIG. 6, axles 35 and 37 may be provided with enlarged tapered head portions, 41 and 43, respectively, in order to secure guide member 9 between leg portions 5 and 7. It is also preferable that apertures 39 be of circular configuration and axles 35 and 37 be of cylindrical configuration, but of smaller diameter than that of apertures 39 in order to permit free pivotal movement of guide member 9 with respect to leg portions 5 and 7. This pivotal movement is demonstrated in FIG. 4 wherein base portion 3 and leg portions 5 and 7 are shown in phantom lines pivoted away from a horizontal position in the clockwise direction while guide member 9 remains stationary.

As evident from FIGS. 1 and 5, engagement of syringe 11 within limiter 1 in the position indicated serves to secure plunger 23 to base portion 3 and render plunger 23 immovable. However, because barrel 13 is freely slidable through passageway 33 of guide member 9, barrel 13 is therefore permitted to move relative to plunger 23 within the distance defined between guide member 9 and base portion 3. For example, in the position of syringe 11 as shown in FIG. 1, plunger 23 is fully retracted within barrel 13 and flange 21 of barrel 13 is therefore disposed in its closest position adjacent base portion 3. As seen in FIG. 2, barrel 13 has been slid through passageway 33 in the left direction to the extent permitted by the position of guide member 9 and the engagement of flange 21 thereagainst. This latter position produces a corresponding extension of plunger 23, and thereby permits syringe 11 to contain a corresponding amount of medication, indicated generally at M. It is therefore apparent that the extended position of plunger 23 relative to barrel 13 is limited by the position of guide member 9, which position may be selectively determined by the user.

It is preferred that base portion 3 and associated leg portions 5 and 7 of limiter 1 be entirely integrally formed, such as by injection molding, of durable plastic material having sufficient resiliency to permit leg portions 5 and 7 to be easily displaced laterally. Guide member 9 and its associated axles 35 and 37 are also preferably integrally molded of durable plastic material of sufficient rigidity to permit enlarged head portions 41 and 43 to be repeatedly snap-fitted through and removed from corresponding pairs of apertures 39. Limiter 1 or portions thereof may of course also be formed in any manner and from any material well known in the art and deemed suitable for the practice of the invention as disclosed herein.

MODE OF OPERATION

The preferred manner in which limiter 1 may be utilized shall now be described with general reference to the drawings. Guide member 9 is first removed from limiter 1 and slid onto the barrel 13 of syringe 11 until it engages flange 21. Syringe 11 is then utilized for withdrawing a desired amound of medication by inserting needle 19 into a conventional medication bottle (not shown) and extending plunger 23 to the desired setting of graduations 15 on barrel 13. Handle 31 of plunger 23 is then engaged within slot 31 of base portion 3, and axles 41 and 43 of guide member 9 are then snap-fitted through a pair of apertures 39 corresponding to the relative position of plunger 23 with respect to barrel 13. In this manner, syringe 11 is therefore fully engaged within limiter 1.

When it is desired to administer medication M to a patient, the entire assembly procedure may be reversed or, alternatively, it is only merely necessary to disengage handle 25 from slot 31 and pivot leg portions 5 and 7 with respect to guide member 9, and away from barrel 13, in the manner shown in FIG. 4. By maintaining guide member 9 is its preset position, limiter 1 may be used to repeatedly administer the same dosage. Moreover, the unused length of each leg portion 5 and 7 extending from the position of guide member 9 towards the free end thereof may be severed and removed, thereby assuring that the original dosage setting of limiter 1 cannot be changed.

It is also apparent that the versatility of limiter 1 permits the utilization of same in different ways, depending upon procedural and patient requirements. It is also understood that the embodiment of the invention herein shown and described is to be taken as merely a preferred example of the same and that various changes in shape, size, composition and arrangement of parts may be resorted to without departing from the spirit of the invention or scope of the appended claims.

I claim:

1. A syringe dosage limiter for controlling the amount of medication administered by a hypodermic syringe of the type including a barrel provided with an outwardly extending flange and a plunger provided with a handle, which limiter comprises:
   (a) a substantially U-shaped body including a base portion and a pair of leg portions;
   (b) a guide member including a passageway therethrough for slidably receiving the barrel of a syringe and engageable with the outwardly extending flange of the barrel;
   (c) means for permitting the guide member to be detachably and pivotally secured to the leg portions at any one of a plurality of locations spaced therealong; and
   (d) the base portion including means for detachably securing the handle of the plunger thereto.

2. The syringe dosage limiter of claim 1 wherein the means for securing the guide member to the leg portions includes:
   (a) a pair of axles extending laterally from opposite sides of the guide member; and
   (b) a plurality of pairs of corresponding apertures formed in the leg portions and spaced therealong for detachable engagement by the axles of the guide member.

3. The syringe dosage limiter of claim 2 wherein each axle terminates in an enlarged head portion over which the corresponding aperture of each leg portion may be snap-fitted.

4. The syringe dosage limiter of claim 1 wherein the means for securing the plunger handle to the base portion includes a slot formed in the base portion.

5. The syringe dosage limiter of claim 4 wherein the slot is partially defined by a pair of inwardly directed ledges which terminate to define a spacing corresponding substantially to the diameter of the plunger.

6. The syringe dosage limiter of claim 1 wherein the U-shaped body is integrally formed of plastic material.

7. The syringe dosage limiter of claim 1 wherein the guide member is integrally formed of plastic material.

8. The syringe dosage limiter of claim 1 wherein the leg portions are sufficiently flexible to permit their lateral displacement in an outward direction.

* * * * *